(12) United States Patent
Amine

(10) Patent No.: US 12,329,920 B2
(45) Date of Patent: Jun. 17, 2025

(54) BALLOON ANGIOPLASTY INFLATION DEVICE AND METHOD OF PREPARING A BALLOON FOR ANGIOPLASTY

(71) Applicant: Osama Amine, Rutherford, NJ (US)

(72) Inventor: Osama Amine, Rutherford, NJ (US)

( * ) Notice: Subject to any disclaimer, the term of this patent is extended or adjusted under 35 U.S.C. 154(b) by 553 days.

(21) Appl. No.: 17/903,105

(22) Filed: Sep. 6, 2022

(65) Prior Publication Data

US 2024/0075259 A1   Mar. 7, 2024

(51) Int. Cl.
*A61M 25/10* (2013.01)

(52) U.S. Cl.
CPC ...... *A61M 25/104* (2013.01); *A61M 25/1018* (2013.01); *A61M 25/1027* (2013.01); *A61M 25/10185* (2013.11); *A61M 25/1025* (2013.01)

(58) Field of Classification Search
CPC ............ A61M 25/104; A61M 25/1018; A61M 25/1027; A61M 25/10185; A61M 25/1025; A61M 25/10182; A61B 17/12109; A61B 2017/22001
See application file for complete search history.

(56) References Cited

U.S. PATENT DOCUMENTS

| | | | | |
|---|---|---|---|---|
| 458,774 A | * | 9/1891 | Lottridge | A61M 1/772 604/38 |
| 4,583,974 A | * | 4/1986 | Kokernak | A61M 5/31586 604/920 |
| 4,654,027 A | * | 3/1987 | Dragan | A61M 25/10185 604/920 |
| 5,213,115 A | * | 5/1993 | Zytkovicz | A61M 5/488 604/920 |
| 5,306,248 A | * | 4/1994 | Barrington | A61M 25/104 604/920 |

(Continued)

FOREIGN PATENT DOCUMENTS

| | | | | |
|---|---|---|---|---|
| JP | 2012517860 A | * | 8/2012 | ............. A61B 17/24 |
| WO | WO-9744077 A1 | * | 11/1997 | ......... A61B 10/0283 |
| WO | WO-9933515 A2 | * | 7/1999 | ...... A61M 25/10182 |

OTHER PUBLICATIONS

"Balloon preparation for venoplasty." https://www.youtube.com/watch?v=kr27x4-JPN8 [Date accessed: Sep. 29, 2018].

*Primary Examiner* — Tan-Uyen T Ho
*Assistant Examiner* — Osama Nemer
(74) *Attorney, Agent, or Firm* — Michael J. Feigin, Esq.; Feigin and Fridman LLC

(57) ABSTRACT

A balloon angioplasty inflation device and method of inflating a balloon includes a syringe body having a fluid chamber, a plunger slidably disposed within the fluid chamber, and a coupling member coupling the plunger to the syringe body. The plunger includes a plunger valve and a seal including a pressure valve allowing air through the seal. The plunger valve is rotatable between an open position and a closed position to selectively allow air to escape the fluid chamber. The method includes connecting the inflation device to a balloon, drawing the plunger to create a negative pressure to withdraw air from the balloon to the fluid chamber, rotating the plunger valve to the open position to evacuate the air from the fluid chamber, rotating the plunger valve to the closed position to seal the fluid chamber, and inflating the balloon to a desired pressure with a contrast-saline solution.

20 Claims, 3 Drawing Sheets

(56) References Cited

U.S. PATENT DOCUMENTS

| | | | | |
|---|---|---|---|---|
| 5,407,424 A | * | 4/1995 | LaFontaine | A61M 1/63 604/6.12 |
| 5,634,910 A | * | 6/1997 | Kanner | A61M 25/10182 604/210 |
| 6,106,496 A | * | 8/2000 | Arnissolle | A61M 25/10182 604/207 |
| 6,162,165 A | * | 12/2000 | Apple | A61N 5/1002 600/3 |
| 6,471,671 B1 | * | 10/2002 | Urick | A61M 5/5086 604/199 |
| 8,002,754 B2 | * | 8/2011 | Kawamura | A61M 5/31515 604/218 |
| 8,647,115 B2 | * | 2/2014 | Boehm | A61C 5/62 433/90 |
| 8,758,294 B2 | | 6/2014 | Kim et al. | |
| 8,795,219 B1 | | 8/2014 | Al-Rashdan | |
| 9,101,739 B2 | | 8/2015 | Lesch, Jr. et al. | |
| 9,770,577 B2 | * | 9/2017 | Li | A61M 29/02 |
| 10,179,226 B2 | * | 1/2019 | Kanner | A61M 39/22 |
| 10,258,774 B2 | * | 4/2019 | Vitullo | A61M 39/223 |
| 2003/0078538 A1 | | 4/2003 | Neale et al. | |
| 2007/0060878 A1 | * | 3/2007 | Bonnette | A61M 25/0133 604/95.04 |
| 2010/0004706 A1 | * | 1/2010 | Mokelke | A61N 1/37512 607/3 |
| 2021/0154443 A1 | | 5/2021 | Casey | |
| 2023/0099569 A1 | * | 3/2023 | Korotko | A61M 25/10186 606/192 |

\* cited by examiner

BALLOON ANGIOPLASTY INFLATION DEVICE AND METHOD OF PREPARING A BALLOON FOR ANGIOPLASTY

FIELD OF THE DISCLOSED TECHNOLOGY

The disclosed technology relates generally to Balloon Angioplasty. More specifically, the disclosed technology relates to a balloon angioplasty inflation device and a method of inflating a single balloon or two angioplasty balloons for (kissing balloon technique) angioplasty.

BACKGROUND OF THE DISCLOSED TECHNOLOGY

Balloon dilatation catheters are used for a variety of procedures in which a syringe body lumen or vessel is dilated. For example, such catheters are used in angioplasty procedures in which a stenosed region of a vessel, such as the subclavian artery or coronary arteries, is widened by inserting a deflated balloon into the stenosis and then inflating the balloon under pressure to forcibly enlarge the lumen through the vessel. After a brief period of time, the balloon is deflated and removed.

A—Balloon dilation catheters are typically actuated by manual syringes, often called "inflators" (or inflation devices), which use a plunger that is manually advanced using a rod that is threaded into a handle to allow the operator to advance the plunger using very small, controlled increments to inflate a balloon. Some syringes include a pressure gauge located on the syringe itself for monitoring the pressure of the balloon monitor the gauge as he or she tries to also watch an image of the balloon being inflated on a monitor. Further, such catheters typically have elongated flexible tubing to which the balloon is mounted. The tubing includes a stopcock interconnecting a tube extending from the inflation device to the tube and a separate tube extending from the stopcock to the balloon. The stopcock controls the fluid communication between the inflation device and the balloon. The stopcock facilitates the removal of any air present in the balloon itself as well as the inflation device to form a negative pressure system. However, the process for setting up and operating a manual balloon inflation device using a stopcock creates logistical difficulties, allowing more room for error by the user.

Kissing balloons is the standard technique used to tackle branch vessel stenosis. When a vessel branches out and both branches has a lesion, single balloon cannot dilate a lesion optimally. This is because, the side branches not only share a common ostial tissue but also shares plaque material within the walls of main and side vessel. Dilating one vessel alone could result in unpredictable plaque shift. For this the 2 angioplasty balloons have to be inflated simultaneously using 2 inflation devices. Having the main operator holding the 2 angioplasty balloons in position and his assistant using an inflation device while his or her assistant using the second inflation device and coordinating the inflation and deflation together creates logistical difficulties, allowing more room for error by users.

Therefore, there is a need in the art for an inflation device that obviates the necessity of a stopcock and able to inflate two balloons simultaneously to create a simpler more streamlined system.

SUMMARY OF DISCLOSED TECHNOLOGY

The disclosed technology provides a balloon angioplasty inflation device including a barrel-shaped syringe body, a plunger, and a coupling member coupling the plunger to the barrel-shaped body. The barrel shaped body includes an open first end, a closed second end, the open first end opposite the closed second end, an exterior surface, an interior surface, and an inner fluid chamber extending between the first end and the second end, the second end including a first port in fluid communication with the fluid chamber, a second port in fluid communication with the fluid chamber, and a port controller coupled to the first port and the second port selectively enabling fluids to flow from the fluid chamber to the first port, the second port, or both the first port and the second port. The first port connectable to a first balloon catheter. The second port connectable to a second balloon catheter. The plunger is slidably disposed within the fluid chamber of the syringe body and includes a distal end, a proximal end, the distal end opposite the proximal end, a plunger shaft extending between the proximal end and the distal end, a plunger bore extending longitudinally through the plunger shaft from the proximal end to the distal end, a plurality of plunger threads disposed on the plunger shaft, and a plunger valve positioned within the plunger bore and extending from the proximal end to the distal end. The proximal end includes a handle for drawing and depressing the plunger with respect to the fluid chamber. The distal end includes an annular seal including a purge valve selectively allowing air through the seal. The plunger valve is in fluid communication with the fluid chamber and rotatable between an open position and a closed position to selectively fluidly communicate with the seal to allow air from the fluid chamber through the plunger valve to the seal. In the open position the plunger valve is in fluid communication with the seal and in the closed position the fluid communication with the seal is broken. The coupling member is disposed on the open first end and includes coupling threads threadably engaged to the plunger threads to couple the plunger to the syringe body. The plunger is translatable longitudinally with respect to the syringe body by rotating the plunger with respect to the coupling member.

In embodiments, the purge valve of the seal includes a channel extending from an upper surface of the seal through the seal to the plunger bore.

In some embodiments, the plunger valve includes a proximal end adjacent to the proximal end of the plunger and a distal end adjacent to the distal end of the plunger, the distal end including an inlet and an outlet in fluid communication with each other, the inlet in fluid communication with the fluid chamber and the outlet capable of fluidly communicating with the channel to allow air from the fluid chamber through the plunger valve to the channel.

In embodiments, in the open position the outlet is aligned with the channel of the seal thereby forming a fluid communication between the plunger valve and the seal and in the closed position the outlet is not aligned with the channel thereby breaking the fluid communication between the plunger valve and the seal.

In some embodiments, the port controller is operable between three positions, the first position enabling fluid flow between the fluid chamber and the second port, only, the second position enabling fluid flow between the fluid chamber and the first port, only, and the third position enabling fluid flow between the fluid chamber and both the first port and the second port, such as in a kissing balloon technique In certain embodiments, the inflation device further includes a pressure gauge coupled to the fluid chamber, the pressure gauge protruding from the exterior surface of the syringe body.

In embodiments, the coupling member comprises threads disposed on the interior surface of the syringe body.

In some embodiments, the coupling member comprises an annular nut threadably fixed to a perimeter of the first open end.

The present disclosed technology further discloses a method of preparing a balloon for angioplasty using the balloon angioplasty inflation device. The method includes connecting the inflation device including a contrast-saline solution inside the fluid chamber directly to an angioplasty balloon to form a balloon angioplasty system. Next, the method includes drawing the plunger from the closed second end to the first open end to create a negative pressure throughout the balloon angioplasty system from the inflation device to the angioplasty balloon to withdraw any air present in the angioplasty balloon to the fluid chamber. Next, the method includes rotating the plunger valve to the open position to fluidly communicate with the seal to evacuate the air withdrawn from the angioplasty balloon from the fluid chamber and then rotating the plunger valve to the closed position to break fluid communication with the seal and create an air-tight fluid chamber. Lastly, the method includes inflating the angioplasty balloon to desired pressure by depressing the plunger from the first open end toward the second closed end to drive the contrast-saline solution from the fluid chamber to the angioplasty balloon.

In embodiments, the method further includes drawing a contrast solution into the fluid chamber by drawing the plunger from the second closed end toward the first open end prior to connecting the inflation device to the angioplasty balloon and then drawing a saline solution into the fluid chamber by drawing the plunger from the second closed end toward the first open end prior to connecting the inflation device to the angioplasty balloon. The amount of saline solution drawn substantially equals the amount of contrast solution drawn.

In certain embodiments, the amount of contrast solution drawn is in the range of 5-7 cubic centimeters and the amount of saline solution drawn is in the range of 5-7 cubic centimeters.

In some embodiments, the method further includes mixing the drawn saline solution and the drawn contrast solution inside the fluid chamber to form the saline-contrast solution.

In certain embodiments, the method further includes turning the port controller to enable the flow of fluids to either the first port of the second port prior to drawing the contrast solution and the saline solution.

In other embodiments, the plunger valve is turned to the closed position prior to drawing the contrast solution and the saline solution.

In embodiments, the method includes inflating the angioplasty balloon with the contrast-saline solution to a desired pressure.

In some embodiments, the method further includes coupling an extension tube including a first end and a second end to the inflation device by connecting the first end of the extension tube to either the first port or the second port of the syringe body prior to drawing the saline solution and contrast solution, wherein coupling the inflation device to the angioplasty balloon includes attaching the second end of the extension tube to an inflation port of the angioplasty balloon.

In certain embodiments, the method further includes advancing a guide wire into the angioplasty balloon until the guide wire exits an end of the angioplasty balloon, wherein advancing the guide wire into the angioplasty balloon comprises inserting the guidewire into a guidewire lumen port of the angioplasty balloon.

In embodiments, inflating the angioplasty balloon includes threadably translating the plunger longitudinally with respect to syringe body toward the closed second end to pressurize the balloon angioplasty system.

In some embodiments, the method further includes deflating the angioplasty balloon by drawing the plunger from the syringe body from the closed second end toward the first open end.

"Angioplasty" refers to "procedures that utilize balloons to open narrowed blood vessels.", percutaneous angioplasty and liberation therapy; a minimally invasive vascular treatment for blocked or narrowed vessel." "angioplasty balloon" or "balloon" refers to "a catheter including an inflatable balloon at its end; which may move through blood vessels to reach narrowed portions of the blood vessels to restore normal blood flow to that portion of the blood vessel by inflating and expanding the proximate vessel." "Fluid" refers to "a substance, such as a liquid or gas, that can flow, has no fixed shape, and offers little resistance to an external stress." "Fluid communication" refers to "the ability to transfer a fluid between objects; the process of fluids transferring between objects or parts."

Any device or step to a method described in this disclosure can comprise or consist of that which it is a part of, or the parts which make up the device or step. The term "and/or" is inclusive of the items which it joins linguistically and each item by itself. "Substantially" is defined as "at least 95% of the term being described" and any device or aspect of a device or method described herein can be read as "comprising" or "consisting" thereof.

DETAILED DESCRIPTION OF EMBODIMENTS OF THE DISCLOSED TECHNOLOGY

Figures 1A, 1B:
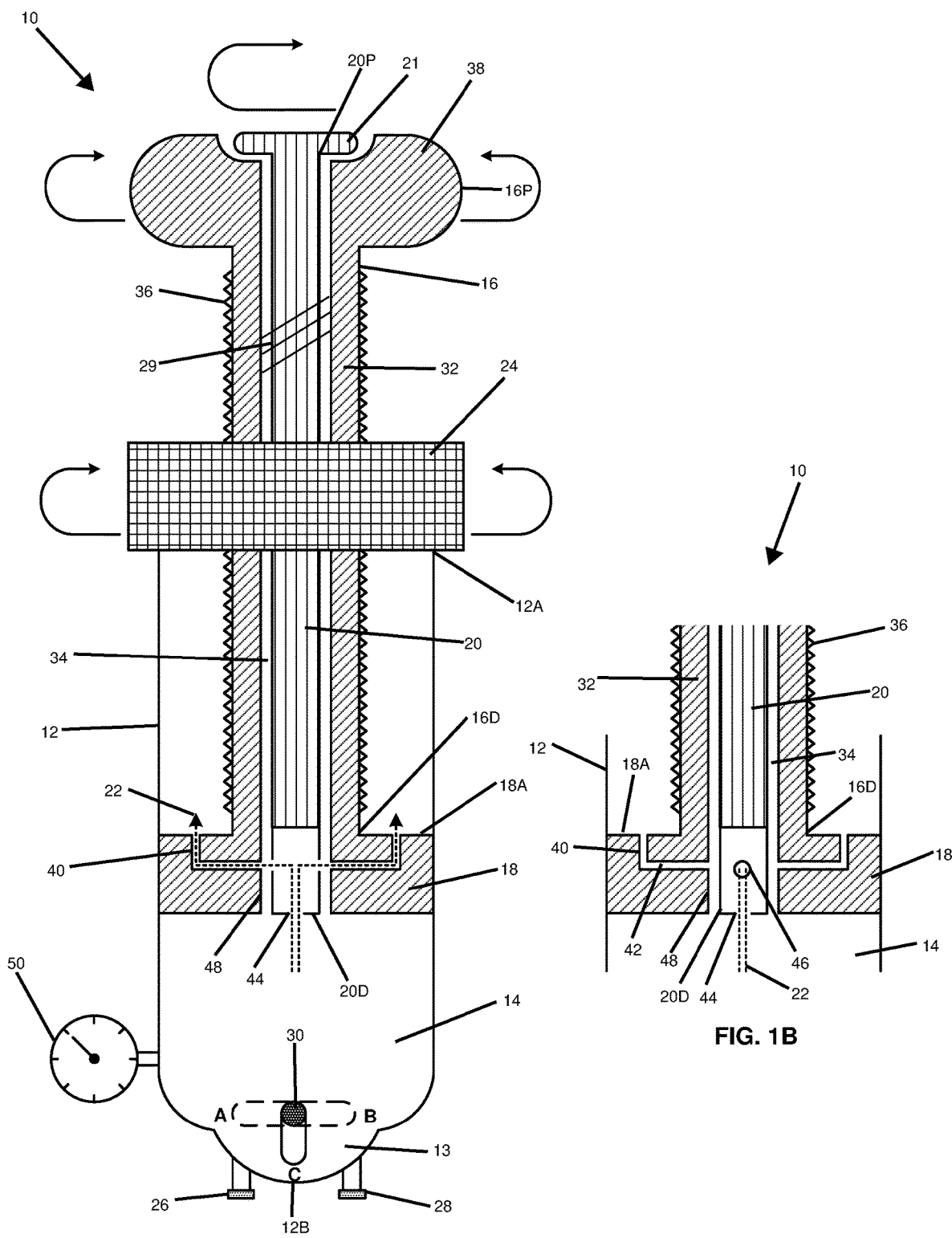
FIG. 1A shows an elevation view of the balloon angioplasty inflation device, illustrating the plunger valve in an open position, fluidly communicating with the seal to release any air present in the fluid chamber according to one embodiment of the present disclosed technology.
FIG. 1B shows a close-up elevation view of the balloon angioplasty inflation device, illustrating the plunger valve in a closed position, breaking the fluid communication with the seal, thereby preventing the release of any air from the fluid chamber according to one embodiment of the present disclosed technology.

Referring now to FIG. 1A and FIG. 1B, FIG. 1A shows an elevation view of the balloon angioplasty inflation device, illustrating the plunger valve in an open position, fluidly communicating with the seal to release any air present in the fluid chamber according to one embodiment of the present disclosed technology. FIG. 1B shows a close-up elevation view of the balloon angioplasty inflation device, illustrating the plunger valve in a closed position, breaking the fluid communication with the seal, thereby preventing the release of any air from the fluid chamber according to one embodiment of the present disclosed technology. The present disclosed technology provides a balloon angioplasty inflation device for use when inflating a balloon for angioplasty. The balloon inflation device 10 comprises a syringe body 12 including an inner fluid chamber 14, a plunger 16 slidably disposed within the fluid chamber 14 and including an annular seal 18 and a plunger valve 20 for enabling the release of air 22 out of the fluid chamber 14, and a coupling member 24 coupling the plunger 16 to the syringe body 12.

In embodiments, the syringe body 12 is barrel-shaped and includes an open first end 12A, a closed second end 12B opposite the open first end 12B, an exterior surface, and an interior surface. The syringe body 12 is transparent enabling a view of the fluid chamber 14 and the interior of the syringe body 12. The open first end 12A defines an opening including a perimeter edge. The closed end 12B is arcuate or U-shaped and may include a bulge 13 for facilitating the transfer of fluids to and from the fluid chamber 14. The fluid chamber 14 extends between the first end 12A and the second end 12B. The second end 12B includes a first port 26 in fluid communication with the fluid chamber 14, a second port 28 in fluid communication with the fluid chamber 14, and a port controller 30 coupled to the first port 26 and the second port 28 for selectively enabling fluids to flow from the fluid chamber 14 to the first port 26, the second port 28, or both the first port 26 and the second port 28. The first port 26 is connectable to a first balloon catheter and/or the tubing thereof and the second port 28 connectable to a second balloon catheter and/or the tubing thereof. The first port 26 and second port 28 include small tubes protruding from the second end 12B. The first and second ports 26, 28 extending downwardly and parallel with respect to the syringe body 12. The port controller 30 is operable between positioned positions to selectively allow the flow of fluids from the fluid chamber 14 to either the first port 26, second port 28, or both the first and second port 26, 28. For example, the first position A enables the fluid flow between the fluid chamber 14 and the second port 28, only. The second position B enables fluid flow between the fluid chamber 14 and the first port 26, only. The third position C enabling fluid flow between the fluid chamber 14 and both the first port 26 and the second port 28. In some embodiments, the first port 26, second port 28, and port controller 30 are disposed on the bulge 13.

The plunger 16 includes a distal end 16D, a proximal end 16P opposite the distal end 16D, a plunger shaft 32 extending between the proximal end 16P and the distal end 16D, a plunger bore 34 extending longitudinally through the plunger shaft 32 from the proximal end 16P to the distal end 16D, a plurality of plunger threads 36 disposed on the plunger shaft 32, and the plunger valve 20, which is positioned within the plunger bore 34 and extends from the proximal end 16P to the distal end 16D. The proximal end 16P includes a handle 38 for drawing and depressing the plunger 16 with respect to the fluid chamber 14. The distal end 16D includes the annular seal 18. The seal 18 includes a pressure valve 40 for selectively allowing the air 22 through the seal 18. The pressure valve 40 comprises a channel 42 extending from an upper surface 18A of the seal 18 through the seal 18 to the plunger bore 34.

The plunger valve 20 is in fluid communication with the fluid chamber 14 and rotatable between an open position and a closed position, as shown by the arrow in FIG. 1A. The plunger valve 20 comprises an elongated member comprising a proximal end 20P and a distal end 20D opposite the proximal end 20P. The proximal end 20P is adjacent to the proximal end 16P of the plunger 16 and includes a handle 21 for rotating and/or pressing down the plunger valve 20 depending on the embodiment of the disclosed technology. In an embodiment of the disclosed technology the plunger vale 20 is threaded with threads 29 such that pressing the handle 21 causes the shaft of the plunger 16 to rotate while being pressed further into plunger valve 20. The distal end 20D is adjacent to the distal end 16D of the plunger 16. The distal end 20D includes an inlet 44 and an outlet 46 in fluid communication with each other. The inlet 44 is in fluid communication with the fluid chamber 14. The outlet 46 is capable of fluidly communicating with the channel 42, by rotation of the plunger valve 20 to the open position, to allow air from the fluid chamber 14 through the plunger valve 20 to the channel 42 and out of the seal 18. Thus, rotation of the plunger valve 20 enables a user to selectively enable fluid communication between the plunger valve 20 and the seal 18 to allow air from the fluid chamber 14 through the plunger valve 20 to the seal 18.

In the open position, the plunger valve 20 is in fluid communication with the seal 18, while in the closed position the fluid communication with the seal 18 is broken. In the open position, the outlet 46 is aligned with the channel 42 of the seal 18 thereby forming a fluid communication between the plunger valve 20 and seal 18. In the closed position, the outlet 46 is not aligned with the channel 42, rather the outlet 46 abuts a wall 48 of the plunger bore 34, thereby breaking the fluid communication between the plunger valve 20 and the seal 18.

The coupling member 24 is disposed on the open first end 12A of the syringe body 12. The coupling member 24 includes coupling threads threadably engaged to the plunger threads 36 to couple the plunger 16 to the syringe body 12. The coupling threads engage the plunger threads 36 by rotating the coupling member 24 with respect to the body 12, as shown in FIG. 1A. The coupling member 24 may be an annular nut threadably fixed to the perimeter edge of the first open end 12A of the syringe body 12. The coupling threads may be disposed on the interior surface of the syringe body 12. The plunger 16 is translatable, or drawable/depressible, longitudinally with respect to the syringe body 12 by rotating the plunger 16 with respect to the coupling member 24, as shown in FIG. 1A.

In embodiments, the balloon angioplasty inflation device further comprises a pressure gauge 50 in communication with the fluid chamber 14 for measuring the barometric pressure within the fluid chamber 14. The pressure gauge 50 may be any known pressure gauge including electronic and non-electronic pressure gauges in the art known to work with balloon inflation devices.

Figure 2A:
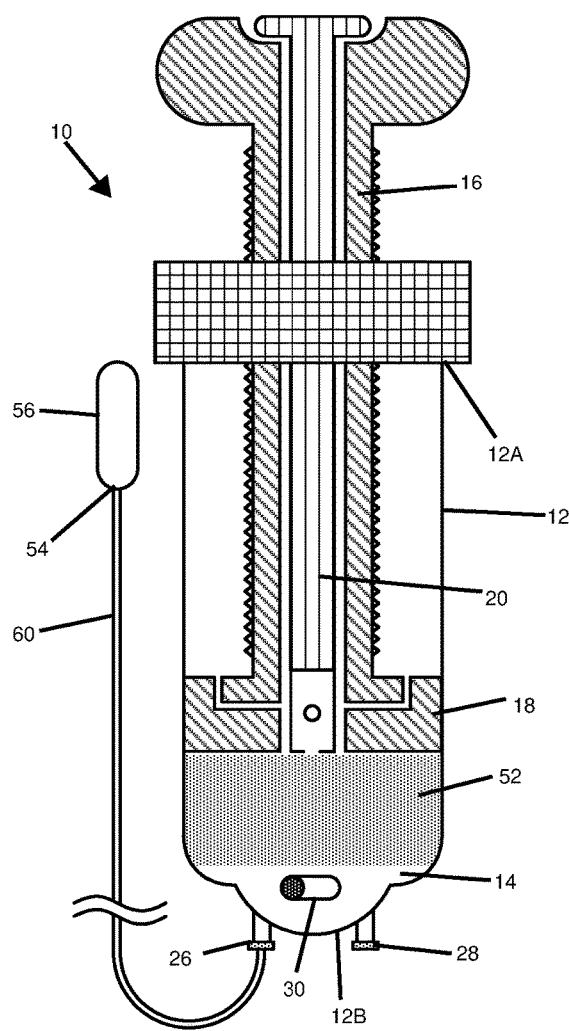
FIG. 2A shows an elevation view of the balloon angioplasty inflation device with a contrast-saline solution in the fluid chamber of the inflation device, illustrating the inflation device connected directly to an angioplasty balloon to form a balloon angioplasty system and further illustrating the angioplasty balloon prior to being prepared for balloon angioplasty according to one embodiment of the present disclosed technology.
Figure 2B:
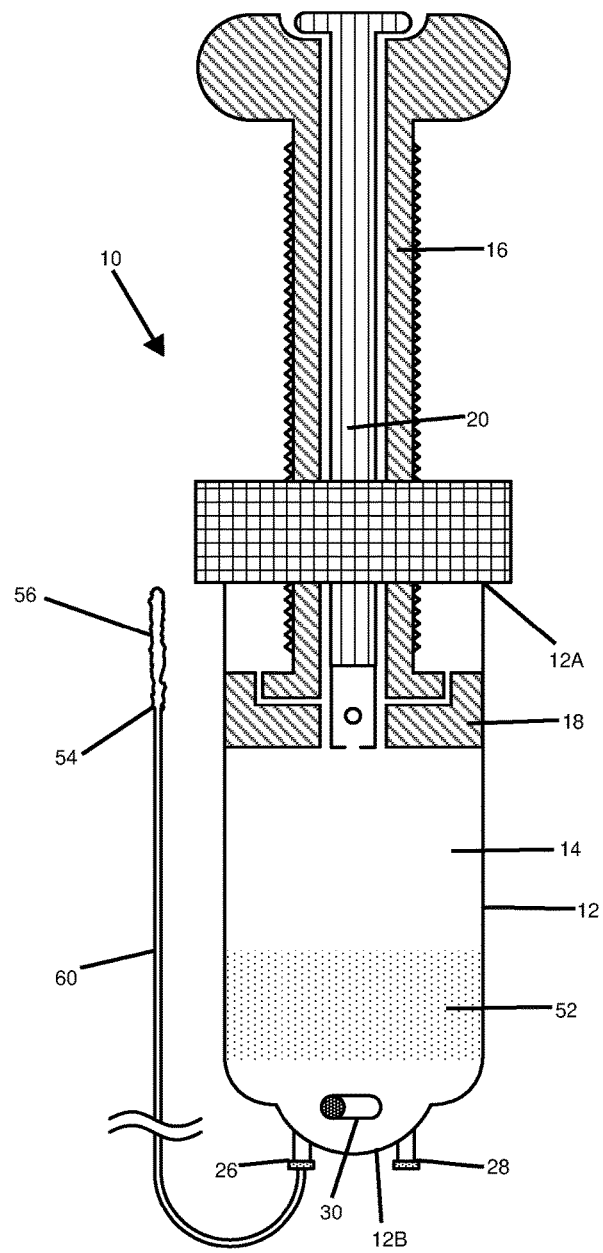
FIG. 2B shows the angioplasty balloon system of FIG. 2A under negative pressure, illustrating the plunger of the inflation device drawn to create the negative pressure and draw any air present in the angioplasty balloon into the fluid chamber of the inflation device according to one embodiment of the present disclosed technology.
Figure 2D:
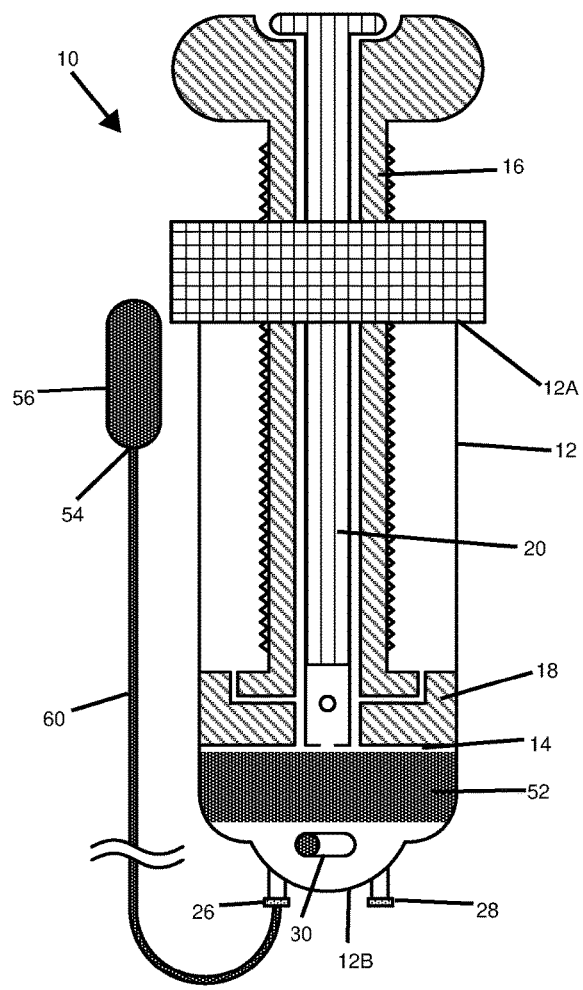
FIG. 2D shows the angioplasty balloon system of FIG. 2A, illustrating the angioplasty balloon inflated to a desired pressure with the saline-contrast solution under pressure and further illustrating the plunger valve in the closed position to enable inflation of the angioplasty balloon to the desired pressure according to one embodiment of the present disclosed technology.
Figure 2C:
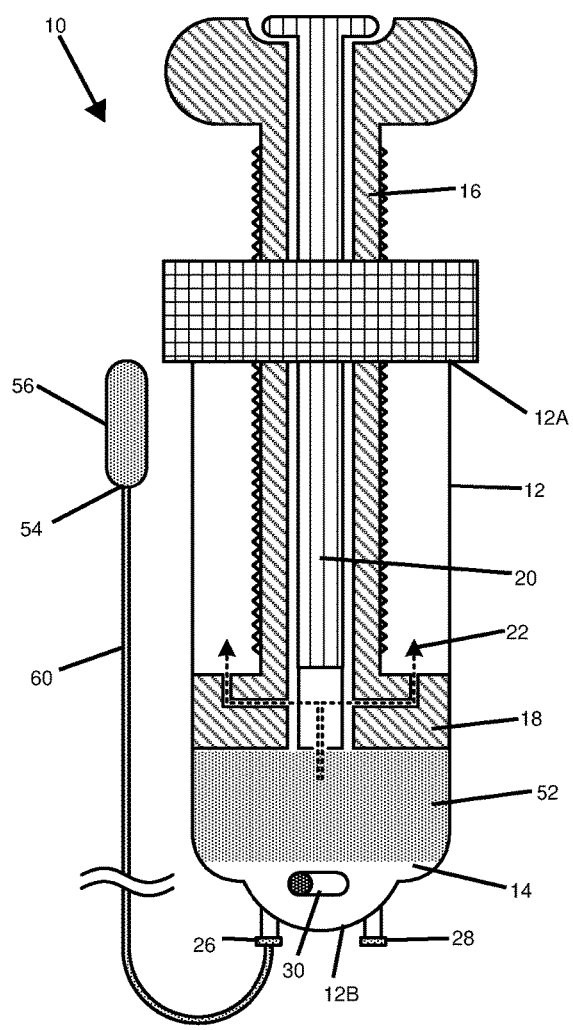
FIG. 2C shows the angioplasty balloon system of FIG. 2A under atmospheric pressure, illustrating the plunger of the inflation device depressed to drive the contrast-saline solution into the angioplasty balloon and fill the angioplasty balloon with the contrast-saline solution and further illustrating the plunger valve in the open position to allow the air drawn from the angioplasty balloon into the fluid chamber to escape from the inflation device according to one embodiment of the present disclosed technology.

Referring now to FIG. 2A, FIG. 2B, FIG. 2C, and FIG. 2D, simultaneously, FIG. 2A shows an elevation view of the balloon angioplasty inflation device with a contrast-saline solution in the fluid chamber of the inflation device, illustrating the inflation device connected directly to an angioplasty balloon to form a balloon angioplasty system and further illustrating the angioplasty balloon prior to being prepared for balloon angioplasty according to one embodiment of the present disclosed technology. FIG. 2B shows the angioplasty balloon system of FIG. 2A under negative pressure, illustrating the plunger of the inflation device drawn to create the negative pressure and draw any air present in the angioplasty balloon into the fluid chamber of the inflation device according to one embodiment of the present disclosed technology. FIG. 2C shows the angioplasty balloon system of FIG. 2A under atmospheric pressure, illustrating the plunger of the inflation device depressed to drive the contrast-saline solution into the angioplasty balloon and fill the angioplasty balloon with the contrast-saline solution and further illustrating the plunger valve in the open position to allow the air drawn from the angioplasty balloon into the fluid chamber to escape from the inflation device according to one embodiment of the present disclosed technology. FIG. 2D shows the angioplasty balloon system of FIG. 2A, illustrating the angioplasty balloon inflated to a desired pressure with the saline-contrast solution under pressure and further illustrating the plunger valve in the closed position to enable inflation of the angioplasty balloon to the desired pressure according to one embodiment of the present disclosed technology.

The present disclosed technology further discloses a method of using the inflation device 10 of the present invention to prepare a balloon for angioplasty. The method includes connecting the inflation device 10 having a contrast-saline solution 52 inside the fluid chamber 14 directly to the lumen/inflation port 54 of an angioplasty balloon 56 to form a balloon angioplasty system, as shown in FIG. 2A. The inflation device 10 may be connected to the angioplasty balloon 56 via the first port 26 or second port 28. The port controller 30 is then switched to the appropriate position to allow fluid communication between the fluid chamber 14 and the angioplasty balloon 56.

In embodiments, where the inflation device 10 is not provided with a contrast-saline solution already in the fluid chamber, the method includes drawing a contrast solution and a saline solution, either together or separately, into the fluid chamber 14 by drawing the plunger 16 from the second closed end 12B toward the first open end 12A prior to connecting the inflation device 10 to the angioplasty balloon 56. Prior to drawing the contrast solution and saline solution, the plunger valve 20 is turned to the closed position. The amount of saline solution drawn substantially equals the amount of contrast solution drawn. In some embodiments, a range of 5-7 cubic centimeters of contrast and a range of 5-7 cubic centimeters of saline are drawn into the fluid chamber 14. Once the saline and contrast solution are drawn into the fluid chamber 14, the saline and contrast are mixed inside the fluid chamber 14 to form the saline-contrast solution 52.

In embodiments, connecting the inflation device 10 to the angioplasty balloon 56 comprises coupling an extension tube 60 to either the first port 26 or the second port 28 of the syringe body 12 and the lumen/inflation port 54 of the angioplasty balloon 56 prior to drawing the saline solution and contrast solution into the fluid chamber 14 of the inflation device 10.

Next, the method includes drawing the plunger 16 from the closed second end 12B to the first open end 12A to create a negative pressure throughout the balloon angioplasty system from the inflation device 10 to the angioplasty balloon 56 to withdraw any air present in the angioplasty balloon 56 to the fluid chamber 14, as shown in FIG. 2B.

Next, the method includes rotating the plunger valve 16 either clockwise or counterclockwise to the open position to fluidly communicate with the seal 18 and evacuate from the fluid chamber 14, the air 22 withdrawn from the angioplasty balloon 56 to the fluid chamber 14, as shown in FIG. 2C. To facilitate evacuation of the air from the fluid chamber 14, the plunger 16 may be depressed toward the closed second end 12B, which forces the air in the fluid chamber 14 out of the seal 18 and some of the contrast-saline solution 52 into the angioplasty balloon, as shown in FIG. 2C.

Next, the method includes rotating the plunger valve 16 to the closed position to break the fluid communication with the plunger valve 16 and the seal 18 and create an air-tight fluid chamber 14, as shown in FIG. 2D.

Lastly, once the plunger valve 20 is closed, the angioplasty balloon 56 is inflated to a desired pressure by depressing the plunger 16 toward the second closed end 12B to drive the contrast-saline solution 52 from the fluid chamber 14 to the angioplasty balloon 56. The angioplasty balloon 56 may be inflated to rated burst pressure. In embodiments, the angioplasty balloon 56 is inflated by threadably translating the plunger 16 longitudinally with respect to syringe body 12 toward the closed second end 12B to pressurize the angioplasty balloon 56.

In embodiments, the method further includes advancing a guide wire into the angioplasty balloon 56 until the guide wire exits an end of the angioplasty balloon 56 by inserting the guidewire into a guidewire lumen port of the angioplasty balloon 56.

In embodiments, the method further includes deflating the angioplasty balloon 56 by drawing the plunger 16 from the syringe body 12 toward the first open end 12A.

Any device or step to a method described in this disclosure can comprise or consist of that which it is a part of, or the parts which make up the device or step. The term "and/or" is inclusive of the items which it joins linguistically and each item by itself.

For purposes of this disclosure, the term "substantially" is defined as "at least 95% of" the term which it modifies.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been disclosed with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

What is claimed is:

1. A balloon angioplasty inflation device, comprising:
    a barrel-shaped syringe body including an open first end, a closed second end, the open first end opposite the closed second end, an exterior surface, an interior surface, and an inner fluid chamber extending between the open first end and the closed second end, the closed second end including a first port in fluid communication with the fluid chamber, a second port in fluid communication with the fluid chamber, and a port controller coupled to the first port and the second port selectively enabling fluids to flow from the fluid chamber to the first port, the second port, or both the first port and the second port, the first port connectable to a first balloon catheter, the second port connectable to a second balloon catheter to be inflated simultaneously using a single inflation device;
    a plunger slidably disposed within the fluid chamber of the syringe body, the plunger including a distal end, a proximal end, the distal end opposite the proximal end, a plunger shaft extending between the proximal end and the distal end, a plunger bore extending longitudinally through the plunger shaft from the proximal end to the distal end, a plurality of plunger threads disposed on the plunger shaft, and a plunger valve positioned within the plunger bore and extending from the proximal end to the distal end, the proximal end including a handle for drawing and depressing the plunger with respect to the fluid chamber, the distal end including an annular seal, the seal including a pressure valve selectively allowing air through the seal, the plunger valve in fluid communication with the fluid chamber and rotatable between an open position and a closed position to selectively fluidly communicate with the seal to allow air from the fluid chamber through the plunger valve to the seal, where in the open position the plunger valve is in fluid communication with the seal and in the closed position the fluid communication with the seal is broken; and
    a coupling member disposed on the open first end, the coupling member including coupling threads threadably engaged to the plunger threads to couple the plunger to the syringe body, the plunger translatable longitudinally with respect to the syringe body by rotating the plunger with respect to the coupling member.

2. The balloon angioplasty inflation device of claim 1, wherein the pressure valve of the seal comprises a channel extending from an upper surface of the seal through the seal to the plunger bore.

3. The balloon angioplasty inflation device of claim 2, wherein the plunger valve comprises a proximal end adjacent to the proximal end of the plunger and a distal end adjacent to the distal end of the plunger, the distal end including an inlet and an outlet in fluid communication with each other, the inlet in fluid communication with the fluid chamber and the outlet capable of fluidly communicating with the channel to allow air from the fluid chamber through the plunger valve to the channel.

4. The balloon angioplasty inflation device of claim 3, where:
    in the open position the outlet is aligned with the channel of the seal thereby forming a fluid communication between the plunger valve and the seal; and
    in the closed position the outlet is not aligned with the channel thereby breaking the fluid communication between the plunger valve and the seal.

5. The balloon angioplasty inflation device of claim 1, wherein the port controller is operable between three positions, the first position enabling fluid flow between the fluid chamber and the second port, only, the second position enabling fluid flow between the fluid chamber and the first port, only, and the third position enabling fluid flow between the fluid chamber and both the first port and the second port.

6. The balloon angioplasty inflation device of claim 1, further comprising a pressure gauge coupled to the fluid chamber, the pressure gauge protruding from the exterior surface of the syringe body.

7. The balloon angioplasty inflation device of claim 1, wherein the coupling member comprises threads disposed on the interior surface of the syringe body.

8. The balloon angioplasty inflation device of claim 1, wherein the coupling member comprises an annular nut threadably fixed to a perimeter of the first open end.

9. A method of preparing a balloon for angioplasty using the balloon angioplasty inflation device of claim 1, comprising:
    connecting the inflation device including a contrast-saline solution inside the fluid chamber directly to an angioplasty balloon to form a balloon angioplasty system;
    drawing the plunger from the closed second end to the first open end to create a negative pressure throughout the balloon angioplasty system from the inflation device to the angioplasty balloon to withdraw any air present in the angioplasty balloon to the fluid chamber;
    rotating the plunger valve to the open position to fluidly communicate with the seal to evacuate the air withdrawn from the angioplasty balloon from the fluid chamber; and
    rotating the plunger valve to the closed position to break fluid communication with the seal and create an airtight fluid chamber.

10. The method of preparing a balloon for angioplasty of claim 9, further comprising:
    drawing a contrast solution into the fluid chamber by drawing the plunger from the second closed end toward the first open end prior to connecting the inflation device to the angioplasty balloon;
    drawing a saline solution into the fluid chamber by drawing the plunger from the second closed end toward the first open end prior to connecting the inflation device to the angioplasty balloon, the amount of saline solution drawn substantially equaling the amount of contrast solution drawn.

11. The method of preparing a balloon for angioplasty of claim 10, further comprising mixing the drawn saline solution and the drawn contrast solution inside the fluid chamber to form the saline-contrast solution.

12. The method of preparing a balloon for angioplasty of claim 10, further comprising turning the port controller to enable the flow of fluids to either the first port for the second port prior to drawing the contrast solution and the saline solution.

13. The method of preparing a balloon for angioplasty of claim 12, wherein the plunger valve is turned to the closed position prior to drawing the contrast solution and the saline solution.

14. The method of preparing a balloon for angioplasty of claim 9, further comprising inflating the angioplasty balloon with the contrast-saline solution to a desired pressure.

15. The method of preparing a balloon for angioplasty of claim 9, further comprising:
    coupling an extension tube including a first end and a second end to the inflation device by connecting the first end of the extension tube to either the first port or the second port of the syringe body prior to drawing the saline solution and contrast solution, wherein coupling the inflation device to the angioplasty balloon includes attaching the second end of the extension tube to an inflation port of the angioplasty balloon.

16. The method of preparing a balloon for angioplasty of claim 9, further comprising advancing a guide wire into the angioplasty balloon until the guide wire exits an end of the angioplasty balloon.

17. The method of preparing a balloon for angioplasty of claim 16, wherein advancing the guide wire into the angioplasty balloon comprises inserting the guidewire into a guidewire lumen port of the angioplasty balloon.

18. The method of preparing a balloon for angioplasty of claim 9, wherein inflating the angioplasty balloon comprises threadably translating the plunger longitudinally with respect to the syringe body toward the closed second end to pressurize the balloon angioplasty system.

19. The method of preparing a balloon for angioplasty of claim 9, further comprising deflating the angioplasty balloon by drawing the plunger from the syringe body from the closed second end toward the first open end.

20. The method of preparing a balloon for angioplasty of claim 10, wherein:
- the amount of contrast solution drawn is in a range of 5-7 cubic centimeters; and
- the amount of saline solution drawn is in a range of 5-7 cubic centimeters.

\* \* \* \* \*